(12) United States Patent
Yu et al.

(10) Patent No.: US 7,705,528 B2
(45) Date of Patent: Apr. 27, 2010

(54) AROMATIC MONOMER-AND CONJUGATED POLYMER-METAL COMPLEXES

(75) Inventors: Wanglin Yu, Midland, MI (US); James J. O'Brien, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 971 days.

(21) Appl. No.: 10/893,182

(22) Filed: Jul. 16, 2004

(65) Prior Publication Data

US 2005/0031900 A1 Feb. 10, 2005

Related U.S. Application Data

(60) Provisional application No. 60/492,434, filed on Aug. 4, 2003.

(51) Int. Cl.
*H01L 51/54* (2006.01)
*H05B 33/14* (2006.01)
*C09K 11/06* (2006.01)
*C08G 79/00* (2006.01)

(52) U.S. Cl. .................. 313/504; 313/506; 257/40; 257/E51.038; 257/E51.044; 428/690; 428/917; 528/9; 528/394; 528/395

(58) Field of Classification Search ............ 528/9, 528/394, 395, 422, 423
See application file for complete search history.

(56) References Cited

U.S. PATENT DOCUMENTS

| | | | | |
|---|---|---|---|---|
| 5,708,130 | A | 1/1998 | Woo et al. ............... | 528/397 |
| 6,169,163 | B1 | 1/2001 | Woo et al. ............... | 528/397 |
| 2002/0034656 | A1 | 3/2002 | Thompson et al. ....... | 428/690 |
| 2002/0193532 | A1 | 12/2002 | Ikehira et al. ........... | 525/333.3 |
| 2003/0091862 | A1* | 5/2003 | Tokito et al. ............ | 428/690 |
| 2004/0135131 | A1* | 7/2004 | Treacher et al. ......... | 252/582 |
| 2004/0247934 | A1* | 12/2004 | Takeuchi et al. ........ | 428/690 |

FOREIGN PATENT DOCUMENTS

| | | |
|---|---|---|
| EP | 1245659 | 10/2002 |
| EP | 1138746 | 5/2004 |
| WO | WO 01/41512 | 6/2001 |
| WO | WO 01/96454 | 12/2001 |
| WO | WO 02/31896 | 4/2002 |
| WO | WO 02/068435 | 9/2002 |
| WO | WO 02/077060 | * 10/2002 |
| WO | WO 02/081488 | 10/2002 |
| WO | WO 03/001616 | 1/2003 |

OTHER PUBLICATIONS

Jiang et al., Organometallics, (1993), vol. 12, No. 4, pp. 1406-1415.*
Treacher et al., WO 02/077060, Certified Translation.*
Macromolecules, vol. 35, No. 19, 2002, Pei et al.
Elsevier M. Schaferling, P. Bauerle/ Synthetic Metals 101 (1999) 38-39, Synthesis and Properties of Porphyrin-functionalized Poly(bithiophenes).
J. Am. Chem. Soc. 1997, 119, 3423-3424, "Photophysics of π-Conjugated Polymers That Incorporate Metal to Ligand Charge Transfer Chromophores".
Elsevier M. J. Cazeca et al./Synthetic Metals 98 (1998) 45-49 "Enhanced performance of polythiophene derivative based light emitting diodes by addition of europium and ruthenium complexes".
Po King Ng et al., Polymer Preparation (1999), 40(2), pp. 1212-1213, "Design and Synthesis of Light Emittiing Conjugated Polymers Functionalized With Transition Metal Complexes".
Jaehyun Kim et al., Polymer Preperation (1999), 40(2), pp. 1237-1238, "Preparation and Properties of Luminescent Metal-Complex Containing Conjugated and Non-Cnjugated Polymers".
Sze Chit Yu, et al. Macromolecules 1999, 32, 5251-5256, "Synthesis, Metal Complex Formation, and Electronic Properties of a Novel Conjugate Polymer with a Tridentate 2, 6-B is (benzimidazol-2-yl) pyridine Ligand".
May 2, 2003 SciFinder, p. 2, Bibliographic Information, "Photophysics of metal-organic π-conjugated polymers". Ley, K.D.; Schanze, K.S. Department of Chemistry, University of Florida, Gainesville, FL, USA. Corrdination Chemistry Reviews (1998), 171 287-307.
May 2, 2003 SciFinder, "Organic Light-emitting diode using Eu3+ polymer complex as an emitter." Zaho et al.,Japanese Journal of Applied Physics, Part 2: Letters (1999).
1999 American Chemical Society Published on Web Mar. 16, 1999, Chem. Mater. 1999, 11, 1165-1170, "Electronic and Light-Emitting Properties of Some Polyimides Based on B is (2,2':6',2"—terpyridine) Ruthenium (II) Complex.", Wai Yue Ng et al.

(Continued)

*Primary Examiner*—D. Lawrence Tarazano
*Assistant Examiner*—Brett A Crouse
(74) *Attorney, Agent, or Firm*—Sughrue Mion, PLLC

(57) ABSTRACT

A halogenated aromatic monomer-metal complex useful for preparing a polymer for electronic devices such as a light-emitting diode (LED) device is described. The aromatic monomer-metal complex is designed to include a linking group that disrupts conjugation, thereby advantageously reducing or preventing electron delocalization between the aromatic monomer fragment and the metal complex fragment. Disruption of conjugation is often desirable to preserve the phosphorescent emission properties of the metal complex in a polymer formed from the aromatic monomer-metal complex. The resultant conjugated electroluminescent polymer has precisely controlled metal complexation and electronic properties that are substantially or completely independent of those of the polymer backbone.

7 Claims, No Drawings

OTHER PUBLICATIONS

J. Mater. Chem., 1999, 9, 2103-2108, "Synthesis and electronic properties of conjugated polymers based on rheinium or ruthenium dipyridophenazine complexes.," Wai Kin Chan, et al.

Journal of Polymer Science: Part A: Polymer Chemistry, vol. 38, 3405-3411 (2000), Copyright 2000 John Wiley & Sons, Inc., "Monochromatic-Red-Light Emission of Novel Copolymers Containing Carbazole Units and Europium-Acrylate Complexes", Muie Yang, et al.

Progress in Inorganic Chemistry, vol. 48, Edited by Kenneth D. Karlin. ISBN 0-471-32623-2 © John Wiley & Sons, Inc., Transition Metals in Polymeric π-Conjugated Organic Frameworks, Richard P. Kingborough et al.

Adv. Mater. 2002, 14, No. 10, May 17, p. 701-707, Fluorescence and Phosphorescence in Organic Materials, Anna Köhler, et al.

J. Am. Chem. Soc. 2001, 123, 8329-8342, Photophysics of π-Conjugated Metal-Organic Oligomers: Aryleneethynylenes that Contain the $(bpy)Re9(CO)_3Cl$ Chromophore, Keith A. Walters, et al.

Chem. Rev. 202, 102, 2357-2368, Organo Lanthanide Metal Complexes for Electroluminescent Materials, Junji Kido, et al.

Inorg. Chem. 2000, 39, 5496-5509, Photophysics and Electron Trnasfer in Poly(3-octylthiophene) Alternating with Ru(II)-Bipyridine Complexes, Keith A. Walters, et al.

J. Am. Chem. Soc. 2001, 123, 9412-9417, The Engery Gap Law for Triplet States in Pt-Containing Conjugated Polymers and Monomers, Joanne S. Wilson et al.

Nature/vol. 413/Oct. 24, 2001/Spin-dependent exciton formation in π-conjugated compounds, J.S. Wilson et al.

Langmuir 2000, 16, 6191-6199, Self-assembled Molecular Architectures on Surfaces: New Strategies Involving Metal-Organic Copolymers, David M. Sarno et al.

Macromolecules, vol. 31, No. 3, 1998, 722-727, Synthesis and Electronic Structure of Platinum-Containing Poly-ynes with Aromatic and Heteroaromatic Rings, N. Chawdhury et al.

S. Lamansky, et al., "Highly Phosphorescent Bis-Cyclometalated Iridium Complex: Synthesis, Photophysical characterization, and Use in Organic Light Emitting Diodes", J. Am. Chem. Soc. 2001, 123, 4303-4312.

S. Lamansky, et al., "Synthesis and Characterization of Phosphorescent Cyclometalated Iridium Complexs", Inorg. Chem. 2001, 40, 1704-1711.

M.A. Baldo, et al., "Very High-efficiency Green Organic Light-emitting devices Based on Electrophosphorescence", Appl. Phys. Lett. 1999, 75, 4-6.

C. Adachi, et al., "High-efficient Red Electrophosphorescence Devices", Appl. Phys. Lett 2001, 78 (11), 1622.

C. Dadachi, et al., "Endothermic Energy Transfer: A Mechanism for Generating Very Efficient High-energy Phosphorescent Emission in Organic Materials", Appl. Phys. Lett. 2001, 79 (13), 2082.

B. W. D' Andrade, et al., "White Light Emission Using Triplet Excimers in Electrophosphorescent Organic Light-Emitting Devices", Adv. Mater. 2002, 14 (15), 1032.

Sh.-Ch. Lo, et al., "Green Phosphorescent Dendrimer for Light-Emitting Diodes", Adv. Mater. 2002, 14 (13-14), 975.

W. Zhu, et al., "Highly Efficient Electrophosphorescent Devices Based on Conjugated Polymers Doped with Iridium Complex", Appl. Phys. Lett. 2002. 80 (12), 2045.

F.-C. Chen, et al., "High-performance Polymer Light-emiting Diodes Doped with a Red Phosphorescent Iriduium Complex", Appl. Phys. Lett. 2002, 80 (13), 2308.

Y. Kawamura, et al., "Energy Transfer in Polymer Electrophosphorescent Light Emitting Devices with Single and Multiple Doped Luminescent Layers", J. Appl. Phys. 2002, 92 (1), 87.

Wanglin Yu, et al., "Aromatic Monomer- and Conjugated Polymer-Metal Complexes", filed Jul. 7, 2004, Co-Pending U.S. Appl. No. 10/885,979.

* cited by examiner

AROMATIC MONOMER-AND CONJUGATED POLYMER-METAL COMPLEXES

CROSS-REFERENCE STATEMENT

This application claims the benefit of U.S. Provisional application No. 60/492,434 filed Aug. 4, 2003.

BACKGROUND OF THE INVENTION

The present invention relates to an aromatic monomer-metal complex, an aromatic polymer-metal complex, which can be prepared from the monomer-metal complex, and an organic electronic device that contains a film of the polymer-metal complex.

Organic electronic devices are found in a variety of electronic equipment. In such devices, an organic active layer is sandwiched between two electrical contact layers; the active layer emits light upon application of a voltage bias across the contact layers.

Polymers containing pendant metal-complex groups constitute a class of polymers suitable for light emitting applications, particularly in active matrix driven polymeric LED displays. These polymers can be prepared, for example, by first polymerizing a monomer containing a ligand capable of complexing with a metal, then contacting the polymer with an organometallic complexing compound to insert the metal center into the polymer bound ligand. For example, in *Macromolecules*, Vol. 35, No. 19, 2002, Pei et al. describes a conjugated polymer with pendant bipyridyl groups directly coordinating with various $Eu^{+3}$ $\alpha,\beta$-diketones.

Similarly, in WO 02/31896, pp 17-18, Periyasamy et al. describes lanthanide metal-complexed polymers prepared by either a one- or two-step synthetic route. In the one-step route, an $ML_n$ emitter is reacted with a polymer having metal-reactive functionality (X) to form a polymer with pendant -X-$ML_{n-1}$ groups. In the two-step route, a polymer with pendant hydroxyethyl functionality is first condensed with a bipyridyl compound containing carboxylic acid functionality to form a polymer containing bipyridyl ester functionality (X-L'), which is then reacted with $ML_n$ to form a polymer with pendant X-L'-$ML_{n-1}$ functionality.

One of the problems with these metal complexed electroluminescent polymers is the incomplete reaction of pendant ligands with the metal complexing reagent. This inefficient coupling results in unpredictability of the properties of the final polymer due to the difficulty in controlling the degree of metal-ligand complexation. Accordingly, it would be advantageous to prepare a luminescent polymer with precisely controlled metal complexation.

SUMMARY OF THE INVENTION

The present invention addresses a need by providing in one aspect a halogenated aromatic monomer-metal complex compound comprising a halogenated aromatic monomer fragment and a metal complex fragment and represented by the following structure:

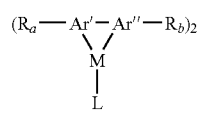

where L is a bidentate ligand; M is Ir, Rh, or Os; Ar' and Ar" are aromatic moieties which may be the same or different with the proviso that at least one of Ar' and Ar" is heteroaromatic; and wherein $R_a$ and $R_b$ are each independently a monovalent substitutent or H, with the proviso that at least one of $R_a$ and $R_b$ contains a halogenated aromatic monomer fragment and a linking group that disrupts conjugation between the halogenated aromatic monomer fragment and the metal complex fragment.

In a second aspect, the present invention is an electroluminescent polymer having a backbone comprising a) structural units of an aromatic monomer-metal complex having an aromatic fragment and a metal complex fragment, which structural units are represented by the following formula:

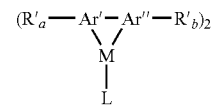

where L is a bidentate ligand; M is Ir, Rh, or Os; Ar' and Ar" are aromatic moieties which may be the same or different with the proviso that at least one of Ar' and Ar" is heteroaromatic; and wherein $R'_a$ and $R'_b$ are substitutents or H, with the proviso that at least one of $R'_a$ and $R'_b$ contains an aromatic group that is part of the polymer backbone and a linking group that disrupts conjugation between the aromatic group and the metal complex fragment; and b) structural units of at least one aromatic comonomer, which polymer is characterized by being conjugated along a polymer backbone created by structural units of the aromatic monomer-metal complex and structural units of the at least one aromatic comonomer.

In a third aspect, the present invention is an electronic device comprising a thin film of a luminescent polymer sandwiched between an anode and a cathode, which luminescent polymer has a backbone with a) structural units of an aromatic monomer-metal complex, which structural units are represented by the following formula:

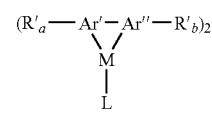

where L is a bidentate ligand; M is Ir, Rh, or Os; Ar' and Ar" are aromatic moieties which may be the same or different with the proviso that at least one of Ar' and Ar" is heteroaromatic; and wherein $R'_a$ and $R'_b$ are substitutents or H, with the proviso that at least one of $R'_a$ and $R'_b$ contains an aromatic group that is part of the polymer backbone and a linking group that disrupts conjugation between the aromatic group and the metal complex fragment; and b) structural units of at least one aromatic comonomer, which polymer is characterized by being conjugated along a polymer backbone created by structural units of the aromatic monomer-metal complex and structural units of the at least one aromatic comonomer.

The present invention addresses a need in the art by providing a simple way of preparing a conjugated electroactive polymer with precisely controlled metal complexation. Moreover, the metal complex groups have electronic and/or luminescent properties that are minimally affected by the conjugated polymer backbone.

DETAILED DESCRIPTION OF THE INVENTION

The first aspect of the present invention is a composition comprising a halogenated aromatic monomer-metal complex having a halogenated aromatic monomer fragment and a metal complex fragment and represented by the following formula:

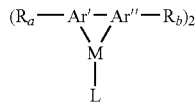

where L is a bidentate ligand; M is Ir, Rh, or Os; Ar' and Ar" are aromatic moieties which may be the same or different with the proviso that at least one of Ar' and Ar" is heteroaromatic; and wherein $R_a$ and $R_b$ are each independently a monovalent substituent or H, with the proviso that at least one of $R_a$ and $R_b$ contains a halogenated aromatic monomer fragment and a linking group that disrupts conjugation between the aromatic monomer fragment and the metal complex fragment.

The halogenated aromatic monomer-metal complex of the present invention can be thought of as comprising a metal complex fragment and one or more halogenated aromatic monomer fragments as illustrated:

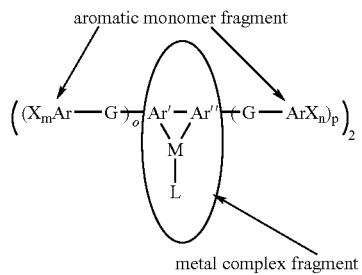

$R_a$ is $X_m$Ar-G- and $R_b$ is $X_n$Ar-G-; each Ar is independently an aromatic group; each G is independently a divalent linking group that disrupts conjugation between Ar and Ar'—Ar", preferably alkylene, O, S, carbonyl, $SiR_2$, where R is a substituent, or oxyalkylene, more preferably methylene, oxymethylene, or O; each X is independently a halogen group, preferably, each X is chloro or bromo; the sum of m+n is a positive integer, preferably 1 or 2; more preferably 1; and the sum of o+p is a positive integer, preferably 1 or 2, more preferably 1. When o (or p) is 0, $R_a$ (or $R_b$) can be any substituent including H. Thus, it is most preferred that each Ar'—Ar" ligand contain one monohalogenated aromatic substituent separated from Ar'—Ar" by conjugation disrupting group.

The ligand Ar'—Ar" is attached at least one substituent that is a polymerizable aromatic monomer separated from the ligand by a divalent linking group. Examples of suitable substituted Ar'—Ar" ligands include, but are not restricted to 2-phenylpyridines, 2-benzylpyridines, 2-(2-thienyl)pyridines, 2-(2-furanyl)pyridines, 2,2'-dipyridines, 2-benzo[b]thien-2-yl-pyridines, 2-phenylbenzothiazoles, 2-(1-naphthalenyl)benzothiazoles, 2-(1-anthracenyl)benzothiazoles, 2-phenylbenzoxazoles, 2-(1-naphthalenyl)benzoxazoles, 2-(1-anthracenyl)benzoxazoles, 2-(2-naphthalenyl)benzothiazoles, 2-(2-anthracenyl)benzothiazoles, 2-(2-naphthalenyl)benzoxazoles, 2-(2-anthracenyl)benzoxazoles, 2-(2-thienyl)benzothiazoles, 2-(2-furanyl)benzothiazoles, 2-(2-thienyl)benzoxazoles, 2-(2-furanyl)benzoxazoles, benzo[h]quinolines, 2-phenylquinolines, 2-(2-naphthalenyl)quinolines, 2-(2-anthracenyl)quinolines, 2-(1-naphthalenyl)quinolines, 2-(1-anthracenyl)quinolines, 2-phenylmethylpyridines, 2-phenoxypyridines, 2-phenylthiopyridines, phenyl-2-pyridinylmethanones, 2-ethenylpyridines, 2-benzenemethanimines, 2-(pyrrol-2-yl)pyridines, 2-(imidazol-2-yl)-pyridines, 2-phenyl-1H-imidazoles, and 2-phenylindoles.

As used herein, "aromatic compounds" includes both aromatic and heteroaromatic compounds unless otherwise stated. Similarly, the term "aryl" is used herein to include both aryl and heteroaryl groups or compounds unless otherwise stated.

The divalent linking group G contains a linking group or atom that disrupts conjugation, thereby inhibiting electron delocalization between the aromatic monomer fragment and the metal complex fragment. This disruption of conjugation between the fragments results in a similar disruption between the complex and the conjugated polymer backbone formed from the aromatic monomer fragment. Disruption of conjugation is often desirable to preserve the light emission properties of the metal complex in a polymer formed from the aromatic monomer-metal complex. Such properties could be disadvantageously perturbed if electrons are delocalized between the conjugated polymer backbone and the complex.

The linking group is preferably a substituted or unsubstituted non-conjugated linear, branched, or cyclohydrocarbylene group or a divalent heteroatom or combinations thereof. Examples of linking groups include, alone or in combination, alkylene or cycloalkyl groups such as methylene, ethylene, propylene, isopropylene, butylene, isobutylene, t-butylene, cyclopropyl, cyclobutyl, cyclopentyl, and cyclohexyl groups; and heteroatoms such as oxygen and sulfur atoms and R—Si—R, carbonyl, and amine groups, except for triaryl amines. Preferred linking groups include an oxygen atom and methylene and oxymethylene groups. As used herein, "oxymethylene" refers to —$OCH_2$— or —$CH_2O$— groups.

General Procedure for Preparation of a Bis(monohalogenated Aromatic) Monomer-Metal Complex A halogenated aromatic monomer-metal complex containing a bis(monohalogenated aromatic) fragment attached to a metal complex through a linking group can be prepared by a 4-step process, as shown:

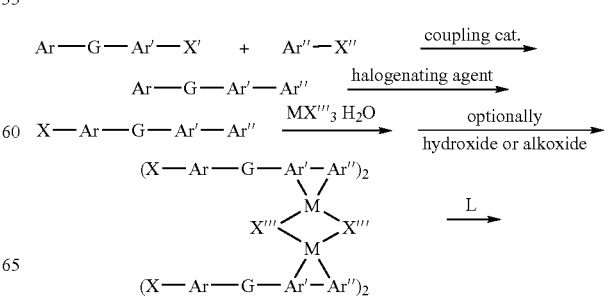

-continued

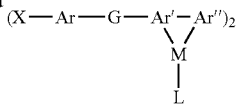

G is as previously defined and is preferably O, methylene, or oxymethylene; Ar, Ar', and Ar" are each independently aromatic moieties with the proviso that at least one of Ar' and Ar" is heteroaromatic. Preferably, Ar is a non-heteroaromatic moiety including a benzene, a naphthalene, or an anthracene moiety, more preferably a benzene moiety. Preferably, Ar' and Ar" are each independently selected from the group consisting of benzene, pyridine, thiophene, and fluorene moieties that are complexed with the metal so as to form a 5-membered ring. More preferably one of Ar' and Ar" is a benzene moiety and the other of a Ar' and Ar" is pyridine moiety.

X is halo, X' and X" are each independently halogen, boronate, —ZnCl, —ZnBr, —MgCl, MgBr, or —Sn($C_{1-10}$-alkyl)$_3$, with the proviso that one of X' and X" is halogen and the other of X' and X" is boronate, —ZnCl, —ZnBr, —MgCl, MgBr, or —Sn($C_{1-10}$-alkyl)$_3$; X''' is halogen, hydroxy, or alkoxy, preferably chloro, bromo, methoxy, or ethoxy, more preferably chloro or bromo. Where X''' is halogen, the addition of the hydroxide or alkoxide base is not necessary; where X''' is hydroxy or alkoxy, the addition of a hydroxide or alkoxide base is preferred.

L is a bidentate ligand which can be the same as or different from Ar'—Ar". Other examples of L include a diamine, including ethylene diamine, N,N,N',N'-tetramethyl ethylene diamine, propylene diamine, N,N,N',N'-tetramethyl propylene diamine, cis- and trans-diaminocyclohexane, and cis- and trans-N,N,N',N'-tetramethyl diaminocyclohexane; an imine, including 2[(1-phenylimino)ethyl]pyridine, 2[(1-(2-methylphenylimino)ethyl]pyridine, 2[(1-(2,6-isopropylphenylimino)ethyl]pyridine, 2[(1-(methylimino)ethyl]pyridine, 2[(1-(ethylimino)methyl]pyridine, 2[(1-(ethylimino)ethyl]pyridine, 2[(1-(isopropylimino)ethyl]pyridine, and 2[(1-(t-butylimino)ethyl]pyridine; a dimine, including 1,2-bis(methylimino)ethane, 1,2-bis(ethylimino)ethane, 1,2-bis(isopropylimino)ethane, 1,2-bis(t-butylimino)ethane, 2,3-bis(methylimino)butane, 2,3-bis(ethylimino)butane, 2,3-bis(isopropylimino)butane, 2,3-bis(t-butylimino)butane, 1,2-bis(phenylimino)ethane, 1,2-bis(2-methylphenylimino)ethane, 1,2-bis(2,6-diisopropylphenylimino)ethane, 1,2-bis(2,6-di-t-butylphenylimino)ethane, 2,3-bis(phenylimino)butane, 2,3-bis(2-methylphenylimino)butane, 2,3-bis(2,6-diisopropylphenylimino)butane, and 2,3-bis(2,6-di-t-butylphenylimino)butane; a heterocyclic compound containing two nitrogen atoms, including 2,2'-bypyridine, and o-phenanthroline; a diphosphine, including bis-(diphenylphosphino)methane, bis-(diphenylphosphino)ethane, bis-(diphenylphosphino)propane, bis-(dimethylphosphino)methane, bis-(dimethylphosphino)ethane, bis-(dimethylphosphino)propane, bis-(diethylphosphino)methane, bis-(diethylphosphino)ethane, bis-(diethylphosphino)propane, bis-(di-t-butylphosphino)methane, bis-(di-t-butylphosphino)ethane, and bis-(di-t-butylphosphino)propane; a 1,3-diketonate (β-diketonate) prepared from a 1,3-diketone (β-diketone), including acetyl acetone, benzoyl acetone, 1,5-diphenylacetyl acetone, dibenzoyl methane, and bis(1,1,1-trifluoroacetyl)methane; a 3-ketonate prepared from a 3-keto ester, including acetoacetic acid ethyl ester; a carboxylate prepared from an aminocarboxylic acid, including pyridine-2-carboxylate, 8-hydroquinolinate, quinoline-2-carboxylate, glycine, dimethyl glycine, alanine, and dimethylaminoalanine; a salicyliminates prepared from a salicylimine, including methyl salicylimine, ethyl salicylimine, and phenyl salicylimine; a dialcoholate prepared from a dialcohol, including ethylene glycol and 1,3-propylene glycol; a dithiolate prepared from a dithiol, including 1,2-ethylene dithiolate and 1,3-propylene dithiolate. Preferably, L is a β-diketonate, pyridine-2-carboxylate, a salicyliminate, or a derivative of 8-hydroquinoline or quinoline-2-carboxylic acid.

Conjugated Luminescent Polymers Containing Metal Complexes

The halogenated aromatic monomer-metal complex is a precursor for a metal-complexed conjugated luminescent polymer, which can be a homopolymer, a copolymer, a terpolymer, etc., and which can be prepared by any of a number of means, For example, the polymer can be prepared by a Suzuki coupling reaction, described in U.S. Pat. No. 6,169,163 (the '163 patent), column 41, lines 50-67 to column 42, lines 1-24, which description is incorporated herein by reference.

In the present case, the Suzuki coupling reaction can be carried out by reacting, in the presence of a catalyst, preferably a Pd/triphenylphosphine catalyst such as tetrakis(triphenylphosphine)palladium(0), the halogenated aromatic monomer-metal complex, preferably the bis(monohalogenated aromatic) complex, with a diboronated aromatic compound. The aromatic group of the co-monomer—which form structural units of the resultant polymer—may be the same as or different from, preferably different from, the aromatic group associated with the halogenated aromatic monomer-metal complex.

It is also possible, and sometimes preferable, to prepare a polymer having structural units of more than two monomers by including in the reaction mixture a variety of halogenated and boronated co-monomers along with the halogenated aromatic monomer-metal complex.

Polymerization can also be carried out by coupling one or more dihalogenated aromatic monomer-metal complexes with one or more dihalogenated aromatic compounds in the presence of a nickel salt, as described in the '163 patent, column 11, lines 9-34, which description is incorporated herein by reference.

The aromatic co-monomers that can be used to couple with the halogenated aromatic monomer-metal complex is nearly endless but a representative list includes, 1,4-diXbenzenes, 1,3-diXbenzenes, 1,2-diXbenzenes 4,4'-diXbiphenyls, 1,4-diXnaphthalenes, 2,6-diXnaphthalenes, 2,5-diXfurans, 2,5-diXthiophenes, 5,5-diX-2,2'-bithiophenes, 9,10-diXanthracenes, 4,7-diX-2,1,3-benzothiadiazoles, diX triarylamines including N,N-di(4-Xphenyl)anilines, N,N-di(4-Xphenyl)-p-tolylamines, and N-diXphenyl-N-phenylanilines, 3,6-diX-N-substituted carbazoles, 2,7-diX-N-substituted carbazoles, 3,6-diX-dibenzosiloles, 2,7-diX-dibenzosiloles, N-substituted-3,7-diXphenothiazines, N-substituted-3,7-diXphenoxazines, diX-N,N,N',N'-tetraaryl-1,4-diaminobenzenes, diX-N,N,N',N'-tetraarylbenzidines, diXarylsilanes, and 2,7-diX-9,9-disubstituted fluorenes, including fluorenes in which the 9,9-substituents combine to form a ring structure, and combinations thereof, where each X is independently a halogen or a boronate, preferably bromo or chloro or boronate, more preferably bromo or boronate. As used herein, "boronate" refers to an aromatic fragment or compound that is substituted with a borane group, a boronic acid ester group, or a boronic acid group.

The resultant polymer has a backbone having structural units of a) an aromatic group which is also attached to a linking group that disrupts conjugation between the aromatic group and the metal complex fragment; and b) an aromatic comonomer, which forms a conjugated system with the aromatic group. The term "structural units" is used herein to refer to the remnant of the monomer after polymerization. A structural unit of the aromatic group that is attached to the metal complex through a linking group is represented by the following structure:

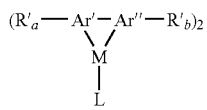

where L, M, Ar', and Ar" are as previously defined, and at least one of $R'_a$ and $R'_b$, preferably only one of $R'_a$ and $R'_b$, contains an aromatic group that is part of the polymer backbone, preferably a phenyl group, a naphthalenyl group, or an anthracenyl group, more preferably a phenyl group; and a linking group, G, that disrupts conjugation between the aromatic group and the metal complex fragment. The other of $R'_a$ and $R'_b$ is preferably a monovalent substituent, including H. Thus, where Ar is phenyl and $R'_b$ is H, the following structural unit is formed:

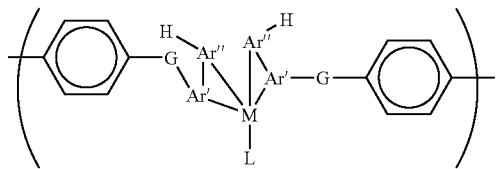

Similarly, a structural unit of a benzene-containing comonomer that is incorporated into the polymer backbone through the 1,4-positions is a 1,4-phenylene group; a structural unit of a 9,9-disubstituted fluorene-containing comonomer that is incorporated into the polymer backbone through the 2,7-positions is a 9,9-disubstituted fluorene-2,7-diyl group, where each R is a substituent, as illustrated:

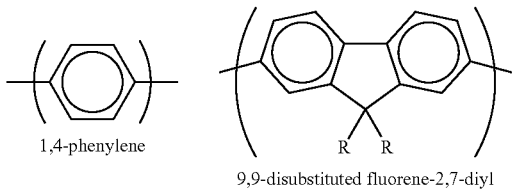

1,4-phenylene 9,9-disubstituted fluorene-2,7-diyl

Accordingly, the structural units corresponding to the above listed co-monomers are 1,4-phenylenes, 1,3-phenylenes, 1,2-phenylenes, 4,4'-biphenylenes, naphthalene-1,4-diyls, naphthalene-2,6-diyl, furan-2,5-diyls, thiophene-2,5-diyls, 2,2'-bithiophene-5,5-diyls, anthracenes-9,10-diyls, 2,1,3-benzothiadiazoles-4,7-diyls, N-substituted carbazole-3,6-diyls, N-substituted carbazole-2,7-diyls, N-substituted-phenothiazine-3,7-diyls, N-substituted-phenoxazines-3,7-diyls, triarylamine-diyls including triphenylamine-4,4'-diyls, diphenyl-p-tolylamine-4,4'-diyls, and N,N-diphenylaniline-3,5-diyls, dibenzosilole-3,6-diyls, dibenzosilole-2,7-diyls, N,N,N',N'-tetraaryl-1,4-diaminobenzene-diyls, N,N,N',N'-tetraarylbenzidine-diyls, arylsilane-diyls, and 9,9-disubstituted fluorenes-2,7-diyls. It is to be understood that the polymer, copolymer, etc. is not limited by the manner in which it is made.

The resultant polymer has a conjugated backbone with metal complexation that can be precisely controlled because preferably at least 90%, more preferably at least 95%, and most preferably 100% of the structural units of the aromatic monomer-metal complex contain a metal complex that is incorporated within the polymer backbone. Moreover, the metal complex is insulated from the conjugated polymer backbone due to the absence of direct delocalization between the ligand and the polymer backbone, which insulation preserves the luminescent properties of the metal complex. The terms "conjugated polymer" and "conjugated polymer backbone" are used to mean that the polymer backbone has electrons that are delocalized throughout at least two adjacent structural units, preferably at least five adjacent structural units, more preferably at least ten adjacent structural units.

Preferably, the ratio of structural units of halogenated aromatic monomer-metal complex to structural units of the comonomer is preferably at least 0.01:99.99, more preferably at least 0.1:99.9, and most preferably at least 1:99; and preferably not greater than 20:80, more preferably not greater than 10:90.

The polymer of the present invention preferably has a weight average molecular weight $M_w$ of at least 5000 Daltons, more preferably at least 10,000 Daltons, more preferably at least 50,000 Daltons, and most preferably at least 100,000 Daltons; and preferably less than 2,000,000 Daltons. $M_w$ is determined using gel permeation chromatography against polystyrene standards.

The polymer of the present invention can be combined with one or more other polymers to make a blend. Examples of suitable blending polymers include homo- or co-polymers (including terpolymers or higher) of polyacrylates, polymethacrylates, polystyrenes, polyesters, polyimides, polyvinylenes, polycarbonates, polyvinyl ethers and esters, fluoropolymers, polycarbazoles, polyarylene vinylenes, polyarylenes, polythiophenes, polyfurans, polypyrroles, polypyridines, polyfluorenes, and combinations thereof.

The polymer or blend of the present invention can be combined with a sufficient amount of one or more solvents (hereinafter "solvent") to make a solution which is useful, for example, as an ink. The amount of solvent varies depending upon the solvent itself and the application, but is generally used at a concentration of at least 80 weight percent, more preferably at least 90 weight percent, and most preferably at least 95 weight percent, based on the weight of the luminescent polymer, the optional additives or modifiers, and the solvent.

Examples of suitable solvents for the polymer include benzene; mono-, di- and trialkylbenzenes including $C_{1-12}$-alkyl benzenes, xylenes, mesitylene, cyclohexylbenzene, and diethylbenzene; furans including tetrahydrofuran and 2,3-benzofuran; 1,2,3,4-tetrahydronaphthalene; cumene; decalin; durene; chloroform; limonene; dioxane; alkoxybenzenes including anisole, and methyl anisoles; alkyl benzoates including methyl benzoate; biphenyls including isopropyl biphenyl; pyrrolidinones including cyclohexylpyrrolidinone; imidazoles including dimethylimidazolinone; and fluorinated solvents; and combinations thereof. More preferred solvents include $C_{1-8}$-alkyl benzenes, cyclohexylbenzene, xylenes, mesitylene, 1,2,3,4-tetrahydronaphthalene, methyl benzoate, isopropyl biphenyl, and anisole, and combinations thereof.

In a typical application, the ink formulation can be deposited on a substrate such as indium-tin-oxide (ITO) glass having a hole transporting material disposed thereon. The solvent is then evaporated, whereupon the ink forms a thin film of the luminescent polymer. The film is used as an active layer in an organic light-emitting diode (OLED) device, which can be used to make a display such as a self-emissive flat panel display. The film is also useful in other electronic devices including light sources, photovoltaic cells, and field effect transistor devices.

The following examples are for illustrative purposes only and are not intended to limit the scope of the invention.

EXAMPLE 1

Preparation of Iridium (III) bis{2-[4'-(4"-bromophenoxy)phenyl]pyridinato-N,$C^{2'}$}(acetylacetonate A. Preparation of 2-(4'-Phenoxy)phenylpyridine 4-Phenoxyphenylboronic acid (10.7 g, 0.05 mol) and 2-bromopyridine (11.58 g, 0.075 mol) were dissolved in 250 mL of THF followd by addition of 2M $NaCO_3$ (60 mL) and tetrakis(triphenylphosphine)palladium (0) (0.29 g). The reaction mixture was boiled at reflux overnight and then transferred into a separation funnel to remove the aqueous layer. The organic layer was removed in vacuo and the residue was eluted through a silica gel column, first with 1:1 chloroform and hexane mixture and then with pure chloroform to afford a pale yellow oil. HPLC showed a purity of 99.5%. GCMS: $M^+$=247.

B. Preparation of 2-[4'-(4"-Bromophenoxy)phenyl]pyridine

A solution of N-bromosuccinimide (NBS, 3.95 g, 22.2 mmol) in DMF (10 mL) was added to a solution of 2-(4'-Phenoxy)phenylpyridine (5.8 g, 23.4 mmol) in DMF (100 mL) at room temperature. The reaction mixture was stirred at 80° C. for 1 h. HPLC showed about 40% of the starting material was converted. Additional NBS (1.55 g) was added and the reaction continued at 80° C. overnight. HPLC indicated a conversion of ~55%. Additional NBS (5 g) was added and the reaction was continued at 80° C. for 1 h. HPLC showed complete conversion of the starting material. After being cooled to room temperature, the reaction mixture was poured into water (300 mL) with stirring whereupon NaOH solution (15 mL of 50% (w/w)) was added into the mixture. The mixture was stirred at room temperature for 2 h and was then filtered to collect the solid. The solid was washed with water and was re-crystalized from ethanol to provide 5.5 g of the titled compound in white crystals. HPLC showed a purity of 98.6%. GCMS: $M^+$=327.

C. Preparation of Iridium (III) bis{2-[4'-(4"-bromophenoxy)phenyl]pyridinato-N,$C^{2'}$} μ-chloro-bridged dimer Iridium (III) chloride (% Ir=54.11, 1.5 g, 4.25 mmol) and 2-[4'-(4"-bromophenoxy)phenyl]pyridine (3.5 g) were dispersed in 2-ethoxyetanol (30 mL) at room temperature. The mixture was boiled at reflux under nitrogen for 20 h, at which time, a yellow solid precipitated from solution. Methanol (100 mL) was added to the reaction mixture to complete the precipitation. The solid was collected by filtration and was washed with methanol, 1N HCl, and ethanol successively and then was dried in vacuo at 40° C. to provide 3.27 g of yellow powder.

D. Preparation of Iridium (III) bis{2-[4'-(4"-bromophenoxy)phenyl]pyridinato-N,$C^{2'}$}(acetylacetonate)

Iridium (III) bis{2-[4'-(4"-bromophenoxy)phenyl]pyridinato-N,$C^{2'}$} μ-chloro-bridged dimer (1.05 g, 0.6 mmol) and sodium carbonate (1.0 g) were dispersed in 2-ethoxyethanol (60 mL). The mixture was degassed with nitrogen at room temperature for 15 min, whereupon 2,4-pentanedione (0.132 g, 1.32 mmol) was added together with 2-ethoxyethanol (20 mL). The mixture was refluxed for 1 h. TLC showed no dimer starting material and the main product was found to be a green emissive material. After being cooled to room temperature, water (100 mL) was added to precipitate the product. The yellow solid was collected by filtration and dried in vacuo at 40° C. overnight. The crude product was re-dissolved in methylene chloride and purified on a silica gel column eluted by methylene chloride to give 0.48 g of yellow powder, purtiy of 99.5% by HPLC.

EXAMPLE 2

Preparation of a Co-polymer Containing Iridium (III) bis[2-(4'-phenoxyphenyl)pyridinato-N,$C^{2'}$](acetylacetonate)

Tetrakis(triphenylphosphine)palladium(0) (5 mg) and 2M aqueous sodium carbonate solution (11 mL) were added under nitrogen to a stirred mixture of 9,9-di(1-octyl)fluorene-2,7-diboronic acid ethylene glycol ester (2.149 g, 4.04 mmol), 2,7-dibromo-9,9-di(1-octyl)fluorene (1.647 g, 3.00 mmol), 3,7-dibromo-N-(4-n-butyl)-phenyl-phenoxazine (0.190 g, 0.40 mmol), N,N'-(di(bromophenyl)-N,N'-di(9,9-dibutyl)fluorene-1,4-phenylenediamine (0.390 g, 0.40 mmol), iridium (III) bis{2-[4'-(4"-bromophenoxy)phenyl] pyridinato-N,$C^{2'}$}(acetylacetonate) (0.188 g, 0.20 mmol), and Aliquat 336 (0.75 g) phase transfer catalyst in toluene (50 mL). The reaction mixture was stirred at 101° C. under nitrogen for 16 h. Then, 9,9-di(1-octyl)fluorene-2,7-diboronic acid ethylene glycol ester (20 mg) was added and the polymerization was continued under the same conditions for another 3 h. Bromobenzene (0.15 g dissolved in 10 mL of toluene) was then added under the same reaction conditions for 2 h. Phenylboronic acid (0.4 g) and tetrakis(triphenylphosphine)palladium(0) (3 mg dissolved in 10 mL of toluene) was added under the same reaction conditions for 4 h. The mixture was allowed to cool to about 50° C., the aqueous layer removed, and the organic layer washed with water. The resultant polymer solution was then poured into methanol (1.5 L) with stirring to precipitate pale yellow polymer fibers. These fibers were collected by filtration, washed with methanol, and dried in vacuo at 50° C. overnight. The polymer was re-dissolved in toluene and the solution passed through a column packed with layers of celite and silica gel. The combined eluates were concentrated to about 100 mL, then poured into methanol (1.5 L) with stirring. The polymer fibers were collected and dried in vacuo at 50° C. overnight. The polymer was re-dissolved in toluene and re-precipitated in methanol. After further filtration and drying, 2.26 g of pale yellow fibers were obtained. The weight average molecular weight ($M_w$) of the polymer was measured by gel permeation chromatography (GPC) against the polystyrene standards as 121,000 with a polydispersity index ($M_w/M_n$) of 3.78.

EXAMPLE 3

Iridium (III) bis[2-(4'-phenoxyphenyl)pyridinato-N, $C^{2'}$](acetylacetonate) Containing a Fluorene copolymer II The procedure described in Example 2 was followed except that N,N-diphenyl-3,5-dibromoaniline (0.3248 g, 0.80 mmol) was used instead of dibromo-N-(4-n-butyl)-phenylphenoxazine and N,N'-(di(bromophenyl)-N,N'-di(9,9-dibutyl)fluorene-1,4-phenylenediamine (0.390 g, 0.40 mmol); the copolymer II was prepared in the yield of 2.13 g.

EXAMPLE 4

Light-Emitting Devices of a Metal Complex-Containing Polymer

A thin film of poly(ethylenedioxythiophene)/polystyrenesulfonic acid (commercially available from H.C. Starck and BAYTRON™ conducting polyer) was spin-coated on a ITO (indium tin oxide)-coated glass substrate, at a thickness of 80 nm. Then, a film of the metal complex-containing polymer described in Example 3 was spin-coated on the PEDOT film at a thickness of 80 nm from a solution in xylenes. After drying, a thin layer (3 nm) of LiF was deposited on the top of the polymer layer by thermal evaporation, followed by the deposition of a calcium cathode (10-nm thick). An additional aluminum layer was applied by evaporation to cover the calcium cathode. By applying a bias (ITO wired positively) on the resultant device, bluish green light emission was obtained. The electroluminescent spectrum recorded at 200 cd/m$^2$ corresponds to the chromaticity coordinates of (x=0.240, y=0.270) in the CIE 1931 diagram. The brightness of the emission reached 200 cd/m$^2$ at about 13 V with the luminance efficiency of 0.08 cd/A.

What is claimed is:

1. An electroluminescent polymer having a backbone comprising a) structural units of an aromatic monomer-metal complex, which structural units are represented by the following formula:

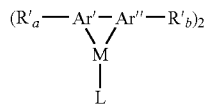

where L is a bidentate ligand; M is Ir, Rh, or Os; Ar' and Ar" are aromatic moieties which may be the same or different with the proviso that at least one of Ar' and Ar" is heteroaromatic; and wherein R'$_a$ and R'$_b$ are substitutents or H, with the proviso that at least one of R'$_a$ and R'$_b$ contains an aromatic group that is part of the polymer backbone and a linking group that disrupts conjugation between the aromatic group and the metal complex fragment; and b) structural units of at least one aromatic comonomer, which polymer is characterized by being conjugated along the polymer backbone created by structural units of the aromatic monomer-metal complex and structural units of the at least one aromatic comonomer.

2. The polymer of claim 1 wherein Ar' and Ar" are each independently selected from the group consisting of benzene, pyridine, thiophene, and fluorene moieties; L is selected from the group consisting of diamines, imines, diimines, heterocyclics containing two nitrogen atoms, diphosphines, β-diketonates, 3-ketonates, salicyliminates, carboxylates, dialcoholates, and dithiolates; R'$_a$ is —Ar-G-, where G disrupts conjugation between Ar and Ar' and is selected from the group consisting of O, S, carbonyl, alkylene, oxyalkylene, and SiR$_2$, where R is a substituent; Ar is selected from the group consisting of phenyl, naphthalenyl, and anthracenyl groups; and wherein the structural units of the at least one aromatic comonomer are selected from the group consisting of 1,4-phenylenes, 1,3-phenylenes, 1,2-phenylenes, 4,4'-biphenylenes, naphthalene-1,4-diyls, naphthalene-2,6-diyls, furan-2,5-diyls, thiophene-2,5-diyls, 2,2'-bithiophene-5,5-diyls, anthracene-9,10-diyls, 2,1,3-benzothiadiazole-4,7-diyls, N-substituted carbazole-3,6-diyls, N-substituted carbazole-2,7-diyls, dibenzosilole-3,6-diyls, dibenzosilole-2,7-diyls, N-substituted-phenothiazine-3,7-diyls, N-substituted-phenoxazine-3,7-diyls, triarylamine-diyls, dibenzosilole-3,8-diyls, dibenzosilole-4,7-diyls, N,N,N',N'-tetraaryl-1,4-diaminobenzene-diyls, N,N,N',N'-tetraarylbenzidine-diyls, arylsilane-diyls, and 9,9-disubstituted fluorene-2,7-diyls and combinations thereof.

3. The polymer of claim 2 wherein one of Ar' and Ar" is a benzene moiety and the other of Ar' and Ar" is a pyridine moiety; L is selected from the group consisting of β-diketonates, pyridine-2-carboxylates, salicyliminates, 8-hydroquinolinates, and quinoline-2-carboxylates; Ar is a phenyl group; and the structural units of the comonomer are selected from any two or more of the group consisting of 9,9-disubstituted fluorene-2,7-diyls, 1,4-phenylenes, N-substituted carbazole-3,8-diyls, N-substituted carbazole-4,7-diyls, N,N-diphenylaniline-3,5-diyls, triphenylamine-4,4'-diyls, diphenyl-p-tolylamine-4,4'-diyls, and N-substituted-phenoxazines-3,7-diyls.

4. A composition comprising the polymer of claim 1 and a solvent for the polymer.

5. The composition of claim 4 wherein the solvent is selected from the group consisting of C$_{1-8}$-alkyl benzenes, cyclohexylbenzene, xylenes, mesitylene, 1,2,3,4-tetrahydronaphthalene, methyl benzoate, isopropyl biphenyl, and anisole, and combinations thereof.

6. The composition of claim 5 which further comprises at least one other polymer that is blended with the electroluminescent polymer.

7. An electronic device comprising a thin film of a luminescent polymer sandwiched between an anode and a cathode, which polymer has a backbone with a) structural units of an aromatic monomer-metal complex, which structural units are represented by the following formula:

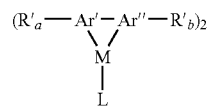

where L is a bidentate ligand; M is Ir, Rh, or Os; Ar' and Ar" are aromatic moieties which may be the same or different with the proviso that at least one of Ar' and Ar" is heteroaromatic; and wherein R'$_a$ and R'$_b$ are substitutents or H, with the proviso that at least one of R'$_a$ and R'$_b$ contains an aromatic group that is part of the polymer backbone and a linking group that disrupts conjugation between the aromatic group and the metal complex fragment; and b) structural units of at least one aromatic comonomer, which polymer is characterized by being conjugated along a polymer backbone created by structural units of the aromatic monomer-metal complex and structural units of the at least one aromatic comonomer.

* * * * *

UNITED STATES PATENT AND TRADEMARK OFFICE
CERTIFICATE OF CORRECTION

| | | |
|---|---|---|
| PATENT NO. | : 7,705,528 B2 | |
| APPLICATION NO. | : 10/893182 | |
| DATED | : April 27, 2010 | |
| INVENTOR(S) | : Wanglin Yu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1265 days.

Signed and Sealed this
Eighteenth Day of January, 2011

David J. Kappos
*Director of the United States Patent and Trademark Office*